United States Patent
Ni et al.

(10) Patent No.: US 11,246,864 B2
(45) Date of Patent: Feb. 15, 2022

(54) COMPOSITIONS AND METHODS OF USING NINTEDANIB FOR TREATING OCULAR DISEASES WITH ABNORMAL NEOVASCULARIZATION

(71) Applicant: ADS Therapeutics LLC, Irvine, CA (US)

(72) Inventors: Jinsong Ni, Irvine, CA (US); Rong Yang, Irvine, CA (US)

(73) Assignee: ADS Therapeutics LLC, Irvine, CA (US)

( * ) Notice: Subject to any disclaimer, the term of this patent is extended or adjusted under 35 U.S.C. 154(b) by 0 days.

(21) Appl. No.: 16/306,152

(22) PCT Filed: May 26, 2017

(86) PCT No.: PCT/US2017/034795
§ 371 (c)(1),
(2) Date: Nov. 30, 2018

(87) PCT Pub. No.: WO2017/210132
PCT Pub. Date: Dec. 7, 2017

(65) Prior Publication Data
US 2020/0323844 A1 Oct. 15, 2020

Related U.S. Application Data

(60) Provisional application No. 62/344,878, filed on Jun. 2, 2016, provisional application No. 62/344,870, filed on Jun. 2, 2016.

(51) Int. Cl.
| | |
|---|---|
| A61K 31/496 | (2006.01) |
| A61K 9/00 | (2006.01) |
| A61P 27/02 | (2006.01) |
| A61K 31/365 | (2006.01) |
| A61K 31/404 | (2006.01) |
| A61K 31/407 | (2006.01) |
| A61K 31/416 | (2006.01) |
| A61K 31/4412 | (2006.01) |
| A61K 31/4439 | (2006.01) |
| A61K 31/444 | (2006.01) |
| A61K 31/4709 | (2006.01) |
| A61K 31/506 | (2006.01) |
| A61K 31/513 | (2006.01) |
| A61K 31/517 | (2006.01) |
| A61K 31/519 | (2006.01) |
| A61K 31/52 | (2006.01) |
| A61K 31/675 | (2006.01) |
| A61K 47/02 | (2006.01) |
| A61K 47/10 | (2017.01) |
| A61K 47/18 | (2017.01) |
| A61K 47/26 | (2006.01) |
| A61K 47/36 | (2006.01) |

(Continued)

(52) U.S. Cl.
CPC .......... *A61K 31/496* (2013.01); *A61K 9/0048* (2013.01); *A61K 9/0051* (2013.01); *A61K 9/08* (2013.01); *A61K 9/107* (2013.01); *A61K 31/365* (2013.01); *A61K 31/404* (2013.01); *A61K 31/407* (2013.01); *A61K 31/416* (2013.01); *A61K 31/444* (2013.01); *A61K 31/4412* (2013.01); *A61K 31/4439* (2013.01); *A61K 31/4709* (2013.01); *A61K 31/506* (2013.01); *A61K 31/513* (2013.01); *A61K 31/517* (2013.01); *A61K 31/519* (2013.01); *A61K 31/52* (2013.01); *A61K 31/675* (2013.01); *A61K 45/06* (2013.01); *A61K 47/02* (2013.01); *A61K 47/10* (2013.01); *A61K 47/183* (2013.01); *A61K 47/186* (2013.01); *A61K 47/26* (2013.01); *A61K 47/36* (2013.01); *A61K 47/40* (2013.01); *A61P 27/02* (2018.01); *A61P 27/06* (2018.01)

(58) Field of Classification Search
CPC .. A61K 31/496; A61K 31/365; A61K 31/404; A61K 31/407; A61K 31/416; A61K 31/4412; A61K 31/4439; A61K 31/444; A61K 31/4709; A61K 31/506; A61K 31/513; A61K 31/517; A61K 31/519; A61K 31/52; A61K 31/675; A61K 47/02; A61K 47/10; A61K 47/183; A61K 47/186; A61K 47/26; A61K 47/36; A61K 47/40; A61K 9/0051; A61K 45/06; A61K 9/0048; A61K 2300/00; A61P 27/02; A61P 27/06
See application file for complete search history.

(56) References Cited

U.S. PATENT DOCUMENTS

| | | |
|---|---|---|
| 8,747,852 B1 | 6/2014 | Pham |
| 9,980,901 B2 | 5/2018 | Ni |

(Continued)

FOREIGN PATENT DOCUMENTS

| | | |
|---|---|---|
| CN | 1247469 | 3/2000 |
| CN | 100455568 | 1/2009 |

(Continued)

OTHER PUBLICATIONS

Masoumpour et al., "Current and future techniques in wound healing modulation after glaucoma filtering surgeries," The Open Ophthalmology Journal, 2016, 10(1):68-85.

(Continued)

*Primary Examiner* — Snigdha Maewall
(74) *Attorney, Agent, or Firm* — Fish & Richardson P.C.

(57) ABSTRACT

Compositions and methods of using nintedanib for treating indications with abnormal neovascularization in the front part of the eye are disclosed.

10 Claims, 2 Drawing Sheets

(51) Int. Cl.

| | | |
|---|---|---|
| *A61K 47/40* | (2006.01) | |
| *A61P 27/06* | (2006.01) | |
| *A61K 9/08* | (2006.01) | |
| *A61K 9/107* | (2006.01) | |
| *A61K 45/06* | (2006.01) | |

(56) References Cited

U.S. PATENT DOCUMENTS

| | | | |
|---|---|---|---|
| 9,987,223 | B2 | 6/2018 | Ni |
| 10,149,820 | B2 | 12/2018 | Ni |
| 10,335,408 | B2 | 7/2019 | Ni et al. |
| 10,688,092 | B2 | 6/2020 | Ni |
| 2008/0003219 | A1 | 1/2008 | Peyman |
| 2008/0268051 | A1 | 10/2008 | Hughes et al. |
| 2012/0315282 | A1 | 12/2012 | Bedinger et al. |
| 2013/0012531 | A1 | 1/2013 | King |
| 2013/0316006 | A1 | 11/2013 | Popov et al. |
| 2013/0324481 | A1* | 12/2013 | Wong .................. A61K 9/0048 514/20.5 |
| 2014/0128395 | A1 | 5/2014 | Ferrari |
| 2014/0186336 | A1 | 7/2014 | Pham |
| 2014/0235678 | A1 | 8/2014 | Böttger et al. |
| 2015/0037422 | A1 | 2/2015 | Kaplan et al. |
| 2015/0038905 | A1 | 2/2015 | Andino et al. |
| 2015/0164790 | A1 | 6/2015 | Bottger et al. |
| 2015/0258120 | A1 | 9/2015 | Zarnitsyn et al. |
| 2015/0265469 | A1 | 9/2015 | Olson |
| 2016/0038760 | A1 | 2/2016 | Hamrah et al. |
| 2017/0020729 | A1 | 1/2017 | Jarrett |
| 2017/0172915 | A1 | 6/2017 | Ni |
| 2017/0209368 | A1 | 7/2017 | Ni |
| 2018/0271780 | A1 | 9/2018 | Ni |
| 2018/0271871 | A1 | 9/2018 | Van Voorhis et al. |
| 2019/0015409 | A1 | 1/2019 | Ni |
| 2019/0110984 | A1 | 4/2019 | Ni |
| 2019/0290643 | A1 | 9/2019 | Ni |

FOREIGN PATENT DOCUMENTS

| | | |
|---|---|---|
| CN | 102018686 | 4/2011 |
| CN | 103212075 | 7/2013 |
| CN | 103764118 | 4/2014 |
| CN | 103889399 | 6/2014 |
| CN | 103998431 | 8/2014 |
| CN | 104379128 | 2/2015 |
| CN | 104379129 | 2/2015 |
| CN | 104379133 | 2/2015 |
| CN | 104448300 | 3/2015 |
| CN | 104884049 | 9/2015 |
| CN | 103732623 | 9/2017 |
| JP | 2014-518064 | 7/2014 |
| JP | 2016-501849 | 1/2016 |
| JP | 2016-040313 | 3/2016 |
| RU | 2351298 | 4/2009 |
| WO | WO 2007/038453 | 4/2007 |
| WO | WO 2012/167143 | 12/2012 |
| WO | WO 2013/188283 | 12/2013 |
| WO | WO 2014/074823 | 5/2014 |
| WO | WO 2014/078655 | 5/2014 |
| WO | WO 2014074823 | 5/2014 |
| WO | WO 2016/029191 | 2/2016 |
| WO | WO 2016/209555 | 12/2016 |
| WO | WO 2016209555 | 12/2016 |
| WO | WO 2017/210130 | 12/2017 |
| WO | WO 2018/022437 | 2/2018 |

OTHER PUBLICATIONS

Supplementary European Search Report in EP Appln. No. 17807295, dated Jan. 29, 2020, 7 pages.
Huu et al., "Light-responsive nanoparticle depot to control release of a small molecule angiogenesis inhibitor in the posterior segment of the eye", J Control Release, 200: 71-77, 2015.
International Search Report and Written Opinion in International Application No. PCT/US17/34795, dated Aug. 27, 2017, 10 pages.
U.S. Appl. No. 15/375,820, filed Dec. 12, 2016, Jinsong Ni.
U.S. Appl. No. 15/474,620, filed Mar. 30, 2017, Jinsong Ni.
U.S. Appl. No. 15/991,382, filed May 29, 2018, Jinsong Ni.
U.S. Appl. No. 15/991,698, filed May 29, 2018, Jinsong Ni.
U.S. Appl. No. 16/210,896, filed Dec. 5, 2018, Jinsong Ni.
U.S. Appl. No. 16/131,945, filed Sep. 14, 2018, Jinsong Ni.
U.S. Appl. No. 16/439,469, filed Jun. 12, 2019, Jinsong Ni.
"Concise Description of Relevance of International Patent Application Publication No. WO 2007/038453 to Pending Claims of U.S. Appl. No. 15/474,620," Third-Party Submission Under 37 CRF 1.290 in U.S. Appl. No. 15/474,620, dated Oct. 20, 2017, 9 pages.
"Concise Description of Relevance of International Patent Application Publication No. WO 2013/188283 to Pending Claims of U.S. Appl. No. 15/474,620," Third-Party Submission Under 37 CRF 1.290 in U.S. Appl. No. 15/474,620, dated Oct. 20, 2017, 8 pages.
"Concise Description of Relevance of International Patent Application Publication No. WO 2016/209555 to Pending Claims of U.S. Appl. No. 15/474,620," Third-Party Submission Under 37 CRF 1.290 in U.S. Appl. No. 15/474,620, dated Oct. 20, 2017, 10 pages.
"Concise Description of Relevance of Roskoski, Biochemical and Biophysical Research Communications 356 (2007) 323-328 to Pending Claims of U.S. Appl. No. 15/474,620," Third-Party Submission Under 37 CRF 1.290 in U.S. Appl. No. 15/474,620, dated Oct. 20, 2017, 2 pages.
"Concise Description of Relevance of Roth et al. J. Med. Chem. (2015) 58, 1053-1063 to Pending Claims of U.S. Appl. No. 15/474,620," Third-Party Submission Under 37 CRF 1.290 in U.S. Appl. No. 15/474,620, dated Oct. 20, 2017, 2 pages.
"Third Party Pre-Issuance Submission Pursuant to 35 U.S.C. § 122(e) and 37 C.F.R. §1.290 for U.S. Appl. No. 15/474,620," Third-Party Submission Under 37 CRF 1.290 in U.S. Appl. No. 15/474,620, dated Oct. 20, 2017, 3 pages.
"Third-Party Submission Under 37 CFR 1.290 Concise Description of Relevance, for U.S. Appl. No. 15/474,620," Third-Party Submission Under 37 CRF 1.290 in U.S. Appl. No. 15/474,620, dated Oct. 20, 2017, 4 pages.
Al-Torbak, "Photodynamic Therapy with Verteporfin for Corneal Neovascularization," Middle East Afr. J. Opthalmol., Apr.-Jun. 2012, 19(2):185-189.
Amoozgar et al., "A role for antimetabolites in glaucoma tube surgery: current evidence and future directions.", Curr Opin Ophthalmol., 27(2): 164-9, 2016.
Amparo et al., "Safety and Efficacy of the Multitargeted Receptor Kinase Inhibitor Pazopanib in the Treatment of Corneal Neovascularization," Investigative Ophthalmology & Visual Science, Jan. 2013, 54(1):537-544.
AVASTIN® Label, Revised Sep. 2011.
Aversa et al., "Linifanib: current status and future potential in cancer therapy", Expert Rev. Anticancer Ther. Early online, 1-11, 2015.
Bayyoud et al., "Cytotoxic Properties of Sunitinib and Sorafenib on Human Corneal Epithelial Cells," Current Eye Research, 2014, 39(2): 149-154.
Bhartiya et al., "The Need to maintain Intraocular Pressure over 24 Hours", Journal of Current Glaucoma Practice, 6(3): 120-123, 2012.
Brandão et al., "Update on Minimally Invasive Glaucoma Surgery (MIGS) and New Implants", Journal of Ophthalmology, 12 pages, 2013.
Chaudhary et al., "XEN Gel Implant: a new surgical approach in glaucoma", Expert Review of Medical Devices, 15:1, 47-59, 2018.
Cox et al., "Doxycycline's Effect on Ocular Angiogenesis: an In Vivo Analysis," Ophthalmology, Sep. 2010; 117(9): 1782-91.
Daniels et al., "Imatinib Treatment for Idiopathic Pulmonary Fibrosis Randomized Placebo-controlled Trial Results", J Respir Crit Care Med vol. 181, pp. 604-610, 2010.
Fossarello et al., "Photodynamic Therapy of Corneal Neovascularization with Verteporfin," Cornea, Jul. 1, 2003, 22(5)485-488.
Fossarello et al., "Photodynamic Therapy of Pterygium With Verteporfin: A Preliminary Report," Cornea, May 2004, 23(4): 330-338.
Gedde et al., "Treatment Outcomes in the Tube Versus Trabeculectomy (TVT) Study After Five Years of Follow-up", Am J Ophthalmol., 153(5): 789-803, 2012.

(56) References Cited

OTHER PUBLICATIONS

Hall et al., "Angiogenesis inhibition as a therapeutic strategy in non-small cell lung cancer (NSCLC)," Transl Lung Cancer Res., Oct. 2015;4(5), 515-23.

Hilberg et al, "BIBF 1120: Triple Angiokinase Inhibitor with Sustained Receptor Blockade and Good Antitumor Efficacy," Cancer Res., Jun. 15, 2008; 68(12):4774-4782.

Hojjat-Farsangi, "Small-Molecule Inhibitors of the Receptor Tyrosine Kinases: Promising Tools for Targeted Cancer Therapies", Int. J. Mol. Sci., 15, 13768-13801, 2014.

Hostettler et al., "Anti-fibrotic effects of nintedanib in lung fibroblasts derived from patients with idiopathic pulmonary fibrosis," Respiratory research, 2014, 15:157.

Hueber et al., "Photodynamic therapy for wound-healing modulation in pterygium surgery. A clinical pilot study," Graefe's Arch Clin Exp Opthalmol, Apr. 2005, 243:942-946.

International Preliminary Report on Patentability in International Application No. PCT/US16/35726, dated Dec. 21, 2017, 10 pages.

International Search Report and Written Opinion in Application No. PCT/US17/34792, dated Oct. 25, 2017, 14 pages.

International Search Report and Written Opinion in International Application No. PCT/US16/35726, dated Sep. 1, 2016, 13 pages.

Jovanovic et al., "The Effect of Topical Doxycycline on Corneal Neovascularization," Current Eye Research, Feb. 1, 2014, 39(2):142-148.

Kaplowitz et al., "Techniques and Outcomes of Minimally-Invasive Trabecular Ablation and Bypass Surgery",Br J Ophthalmol., 98(5): 579-585, 2014.

Kareem et al, 'The use of antimetabolites as adjunctive therapy in fhe surgical treatment of pterygium Clinical Ophthalmology, vol. 6 (Nov. 7, 2012), 6 pages.

Katoh, "FGFR inhibitors: Effects on cancer cells, tumor microenvironment and whole-body homeostasis (Review)", International Journal of Molecular Medicine 38: 3-15, 2016.

Kay et al., "Imatinib Mesylate Treatment of Nephrogenic Systemic Fibrosis", Arthritis & Rheumatism, vol. 58, No. 8, pp. 2543-2548, 2008.

Kitagawa et al., "Activity-based kinase profiling of approved tyrosine kinase inhibitors",Genes to Cells, 18, 110-122, 2013.

Ko et al.,"Inhibition of Corneal Neovascularization by Subconjunctival and Topical Bevacizumab and Sunitinib in a Rabbit Model," Cornea, May 2013;32(5):689-695.

Kumar et al, "Myelosuppression and kinase selectivity of multikinase angiogenesis inhibitors," British Journal of Cancer, Oct. 2009; 101:1717-1723.

Lee et al., "Effect of porcine chondrocyte-derived extracellular matrix on the pterygium in mouse model," Graefes Arch Clin Exp Ophthalmol., Apr. 2014; 252(4):609-618.

Lee et al., "Pivotal role of vascular endothelial growth factor pathway in tumor angiogenesis", ASTR, 8 pages, 2015.

Lucentis® Label, Clinical Trial Date Dec. 2011.

Maddula et al, "Horizons in Therapy for Corneal Angiogenesis," Ophthalmology, Mar. 2011, 118(3):591-599.

OFEV Capsules Approval Letter, Application No. 205832Orig1s000, 8 pages, Approval date Oct. 15, 2014.

Ornitz et al., "The Fibroblast Growth Factor signaling pathway", WIREs Dev Biol., vol. 4, 215-266, 2015.

Perez-Santonja et al., "Inhibition of Corneal Neovascularization by Topical Bevacizumab (Anti-VEGF) and Sunitinib (Anti-VEGF and Anti-PDGF) in an Animal Model," Am J Ophthalmol., Oct. 2010; 150(4):519-528.

Pozarowska et al., "The era of anti-vascular endothelial growth factor (VEGF) drugs in ophthalmology, VEGF and anti-VEGF therapy", Cent. Eur. J. Immunol., 41 (3): 311-316, 2016.

Roskoski Jr., "Sunitinib: A VEGF and PDGF receptor protein kinase and angiogenesis inhibitor," Biochem.Biophys. Res. Comm. (2007) 356:323-328.

Roth et al. "Nintedanib: From Discovery to the Clinic" J. Med. Chem (2015) 58:1053-1063.

Rúa et al., "Oral Doxycycline Reduces Pterygium Lesions; Results from a Double Blind, Randomized, Placebo Controlled Clinical Trial," PLOS ONE, Dec. 2012, 7(12):e52696, 7 pages.

Schlunck et al., "Conjunctival fibrosis following filtering glaucoma surgery.", Exp Eye Res., 142: 76-82, 2016.

Sonoda et al., "ACAID induced by allogeneic corneal tissue promotes subsequent survival of orthotopic corneal grafts.", Invest Ophthalmol Vis Sci., 41(3): 790-8, 2000.

Sonoda et al., "Characterization of cell-mediated immune responses elicited by orthotopic corneal allografts in mice.", Invest Ophthalmol Vis Sci., 36(2): 427-34, 1995.

Third Party Submission Under 37 CFR 1.290 for U.S. Appl. No. 15/474,620, dated Oct. 20, 2017, 3 pages.

U.S. Appl. No. 62/183,180, filed Jun. 22, 2015, 14 pages.

Van Bergen et al., "Inhibition of placental growth factor improves surgical outcome of glaucoma surgery.", J Cell Mol Med., 17(12): 1632-43, 2013.

Vandewalle et al., "Intracameral bevacizumab as an adjunct to trabeculectomy: a 1-year prospective, randomised study.", Br J Ophthalmol., 98(1): 1-6, 2013.

Wollin et al., "Mode of action of nintedanib in the treatment of idiopathic pulmonary fibrosis," Eur. Respir, J., 2015, 45(5):1434-45.

Wong et al., "Matrix metalloproteinase inhibition modulates post-operative scarring after experimental glaucoma filtration surgery.", Invest Ophthalmol Vis Sci., 44(3): 1097-1103, 2003.

Yamagami et al., "The critical role of lymph nodes in corneal alloimmunization and graft rejection.", Invest Ophthalmol Vis Sci., 42(6): 1293-8, 2001.

Yu et al., "High-risk corneal allografts: A therapeutic challenge.", World J Transplant., 6(1): 10-27, 2016.

[No Author Listed], "Clinical Pharmacology and Biopharmaceutics Review(s)," Center for Drug Evaluation and Research, submitted by Boehringer Ingelheim, Inc. on May 2, 2014, 140 pages (Exhibit No. 1026).

[No Author Listed], "EPAR Summary for the Public: Vargatef (nintedanib)," European Medicines Agency, © 2015, 3 pages (Exhibit No. 1013).

[No Author Listed], "OFEV (nintedanib) FDA Label," Boehringer Ingelheim Pharmaceuticals, Inc., © 2014, 18 pages (Exhibit No. 1012).

[No Author Listed], "Standard Affidavit," Internet Archive Standard Affidavit, 2020, 2 pages, retrieved from URL: https://archive.org/legal/affidavit/php, retrieved on Jul. 31, 2020 (Exhibit No. 1029).

[No Author Listed], "Table of Contents," IOVS, 2013, 54(1): 1-24, retrieved from URL: https://web.archive.org/web/20131008205602/http:/www.iovs.org/content/54/1.toc, retrieved on Jul. 30, 2020 (Exhibit No. 1028).

Affidavit of Elizabeth Rosenberg, dated Aug. 5, 2020, 22 pages (Exhibit No. 1030).

*Allgenesis Biotherapeutics Inc.* v. *Cloudbreak Therapeutics, LLC,* "Declaration of Dr. Thomas Malone," Case No. IPR2020-01438, U.S. Pat. No. 10,149,820, dated Aug. 7, 2020, 113 pages (Exhibit No. 1005).

Amparo et al, "Safety and Efficacy of the Multitargeted Receptor Kinase Inhibitor Pazopanib in the Treatment of Corneal Neovascularization," Investigative Ophthalmology & Visual Science, Jan. 2013, 54(1):537-544 (Exhibit No. 1009).

Davis et al., "Comprehensive analysis of kinase inhibitor selectivity," Nautre Biotechnology, 2011, 29(11):1046-1051 (Exhibit No. 1016).

Gougis et al., "Clinical pharmacology of anti-angiogenic drugs in oncology," Critical Reviews in Oncology / Hematology, 2017, 119:75-93 (Exhibit No. 1024).

Gover-Proaktor et al., "Bosutinib, dasatinib, imatinib, nilotinib, and ponatinib differentially affect the vascular molecular pathways and functionality of human endothelial cells," Leukemia & Lymphoma, 2018, 60:189-199 (Exhibit No. 1022).

Inventor Declaration filed during the Prosecution of US Patent Application Publication No. 20130012531 to King et al., dated Sep. 2012, 3 pages (Exhibit No. 1020).

Manallack et al., "The significance of acid/base properties in drug discovery," Chem. Soc. Rev., 2013, 42:485-496 (Exhibit No. 1018).

(56) References Cited

OTHER PUBLICATIONS

Memorandum from Deputy Commisioner from Patent Examination Policy to Patent Examining Corps, dated Apr. 5, 2018, 7 pages (Exhibit No. 1019).
PCT International Publication No. WO 2007038453, published on Apr. 5, 2007, Peyman et al., 54 pages (Exhibit No. 1010).
PCT International Publication No. WO 2016209555, published on Dec. 29, 2016, Nguyen et al., 42 pages (Exhibit No. 1006).
Perez-Santonja et al., "Inhibition of Corneal Neovascularization by Topical Bevacizumab (Anti-VEGF) and Sunitinib (Anti-VEGF and Anti-PDGF) in an Animal Model," Am J Ophthalmol., Oct. 2010, 150(4):519-528 (Exhibit No. 1014).
Prosecution History of U.S. Pat. No. 10,149,820, filed on May 29, 2018, 132 pages (Exhibit No. 1002).
Prosecution History of U.S. Pat. No. 10,154,994, filed on Sep. 11, 2017, 709 pages (Exhibit No. 1015).
Prosecution History of U.S. Pat. No. 9,987,223, filed on Apr. 11, 2017, 562 pages (Exhibit No. 1025).
Response to Office Action in U.S. Appl. No. 16/210,896, filed Apr. 10, 2020, 20 pages (Exhibit No. 1023).
Roskoski Jr., "Classification of small molecule protein kinase inhibitors based upon the structures of their drug-enzyme complexes," Pharmacological Research, 2016, 103:26-48 (Exhibit No. 1017).
Roth et al., "Nintedanib: From Discovery to the Clinic," J. Med. Chem., 2015, 58:1053-1063 (Exhibit No. 1011).
US Patent Application Publication No. 2008/0003219, published on Jan. 3, 2008, Peyman, 11 pages (Exhibit No. 1021).
US Patent Application Publication No. 2013/0012531, published on Jan. 10, 2013, King et al., 13 pages (Exhibit No. 1008).
U.S. Pat. No. 10,149,820, issued on Dec. 11, 2018, Ni, 20 pages (Exhibit No. 1001).
U.S. Appl. No. 62/172,063, filed Jun. 6, 2015, 18 pages (Exhibit No. 1003).
U.S. Appl. No. 62/183,180, filed Jun. 22, 2015, 24 pages (Exhibit No. 1007).
U.S. Appl. No. 62/186,660, filed Jun. 30, 2015, 20 pages (Exhibit No. 1004).
CAS Registry record for NINTEDANIB, retrieved from STN on Aug. 12, 2020.
Extended European Search Report in Application No. 16808064.6, dated Jan. 3, 2019, 8 pages.
Livezeanu et al., "Angiogenesis in the pathogenesis of pterygium", Rom. J. Morph. Embryol, 2011, 837-844.
Chinese Office Action in Chinese Appln. No. 201680042858, dated Oct. 21, 2019, 12 pages (with English translation).
Kria, "Growth factors in cultured pterygium fibroblasts: immunohistochemical and ELISA analysis," Graefe's Arch for Clin. Exp. Ophthalmol., 1998, 236:702-708.
Kria, "Immunohistochemical localization of basic fibroblast growth factor, platelet derived growth factor, transforming growth factor-beta and tumor necrosis factor-a in the pterygium," Acta Histochem, 1996, 98:195-201.
Peng, "Vascular endothelial growth factor gene polymorphism and protein expression in pathogenesis of pterygium," Br J Ophthalmol., 2013, 98:556-561.
Zhang et al., "Correlation of vascular endothelial growth factor and CD105-microvascular density in primary pterygium," J Huazhong Univ Sci Technol., 2011, 31(4):560-564.
Qazi et al., " Corneal allograft rejection: immunopathogenesis to therapeutics," J. Clin Cell. Immunol., 2013, Suppl 9.

\* cited by examiner

COMPOSITIONS AND METHODS OF USING NINTEDANIB FOR TREATING OCULAR DISEASES WITH ABNORMAL NEOVASCULARIZATION

CLAIM OF PRIORITY

This application is a National Stage Application under 35 U.S.C. § 371 and claims the benefit of International Application No. PCT/US2017/034795, filed May 26, 2017, which claims the benefit of U.S. Provisional Patent Application Ser. No. 62/344,878, filed on Jun. 2, 2016 and U.S. Provisional Patent Application Ser. No. 62/344,870, filed on Jun. 2, 2016, the entire contents of each are hereby incorporated by reference.

TECHNICAL FIELD

The present disclosure relates to ocular compositions and methods of using nintedanib for the treatment and prevention of graft rejection in high-risk corneal transplant patients, and for the treatment of eye diseases involving abnormal neovascularization in the front part of the eye.

BACKGROUND

Abnormal neovascularization is involved in many diseases in the front part of the eye. Abnormal neovascularization is involved with graft rejection in high-risk corneal transplant patients. Current treatments for many of these indications need improvements. The methods disclosed herein address the problems in current treatments and provide improved treatments for these diseases.

SUMMARY

In certain aspects, the disclosure provides a method for treating eye diseases involving abnormal neovascularization in the front part of the eye, the method comprising an effective amount of administering nintedanib or a pharmaceutically acceptable salt thereof to the eye of a subject in need of such treatment. In certain aspect, the disclosed methods treat, prevent, or delay onset of graft rejection in corneal transplant patients. For example, the disclosed methods treat, prevent, or delay onset of graft rejection in corneal transplant patients with high risk of graft rejection. In certain aspect, the disclosed methods are performed before operation, in conjunction with operation or after operation, to prevent graft rejection in high-risk corneal transplant.

In certain aspect, nintedanib is administered in the form of a topical ocular formulation administered topically to the affected eye. In certain aspect, the concentration of nintedanib in the formulation is from 0.001% to 10% by weight or by volume the total amount of composition. For example, an aqueous composition comprises 0.001%, 0.01%, 0.1%, 0.5%, 1.0%, 1.5%, 2.0%, 5.0% or up to 10% nintedanib. In certain aspect, the topical ocular formulation is a solution, a suspension, gel, or an emulsion. In another aspect, nintedanib is administered in the form of an implant or semi-solid sustained release formulation injected into the affected eye. In certain aspect, the amount of nintedanib in the implant is from 1 µg to 100 mg.

The term "subject" refers to an animal or human, or to one or more cells derived from an animal or human. Preferably, the subject is a human. Subjects can also include non-human primates. A human subject can be known as a patient.

Unless otherwise defined, all technical and scientific terms used herein have the same meaning as commonly understood by one of ordinary skill in the art to which this invention belongs. Methods and materials are described herein for use in the present invention; other suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DESCRIPTION OF DRAWINGS

FIG. 2A provides results on day 12 and FIG. 2B provides results on day 14. The area of cornea neovascularization are shown for each treatment groups (CBT-1=nintedanibe ocular formlation: 0.2% CBT-1 BID, 0.2% CBT-1 TID; 0.05% CBT-1 BID, 0.0.5% CBT-1 TID; vehicle control TID. T-test significance levels comparing each group vs vehicle are shown by asterisk symbols.

DETAILED DESCRIPTION

Figure 1:
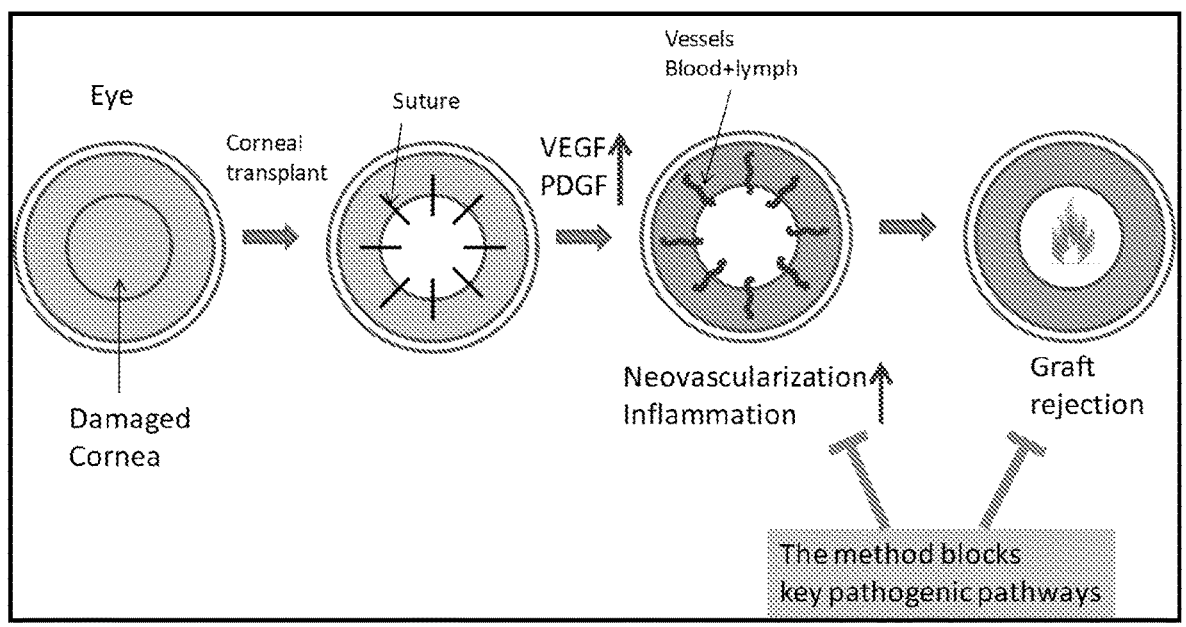
FIG. 1 is a schematic diagram demonstrating an exemplary mechanism to prevent graft rejection in high-risk corneal transplant patients according to the present disclosure.

Corneal transplant is a common surgical procedure. Although the overall success of corneal transplant is good, graft failure is still a problem in some high-risk patients. These patients have high inflammation and neovascularization in the host bed that confers increased immune responses and rejection of allograft (Yu et al. World J Transplant. 2016; 6(1):10-27). Oral immunosuppressive drugs are sometimes used to reduce the risk of graft failure but they have systemic side effects. The disclosed methods will inhibit vascular endothelial growth factor ("VEGF") and platelet-derived growth factor ("PDGFR") mediated excess neovascularization and attenuate VEGF and fibroblast growth factor ("FGF") related immune responses to prevent graft rejection in high-risk patients. The mechanism is illustrated in FIG. 1.

In addition to corneal graft rejection, the disclosed methods can be used to treat any ocular indications involving abnormal neovascularization in the front part of the eye. These indications include graft versus host disease, atopic conjunctivitis, ocular rosacea, ocular pemphigoid, Lyell's syndrome, neovascularization induced by viral, bacterial, fungal, or parasitic infection, contact lens induced neovascularization, ulceration, alkali burns, stem cell deficiency, pinguecula, neovascular glaucoma, dry eye diseases, Sjogren's syndrome, Meibomian gland dysfunction, Steven Johnson syndrome, tumor in the eye.

The terms "treatment", "treating", "treat" and the like are used herein to generally refer to obtaining a desired pharmacologic and/or physiologic effect. The effect can be prophylactic in terms of completely or partially preventing a disease or symptom(s) thereof and/or may be therapeutic in terms of a partial or complete stabilization or cure for a disease and/or adverse effect attributable to the disease. The term "treatment" encompasses any treatment of a disease in a mammal, particularly a human, and includes: (a) preventing the disease and/or symptom(s) from occurring in a subject who may be predisposed to the disease or symptom but has not yet been diagnosed as having it; (b) inhibiting the disease and/or symptom(s), i.e., arresting their development; or (c) relieving the disease symptom(s), i.e., causing regression of the disease and/or symptom(s). Those in need of treatment include those already inflicted (e.g., those with increased corneal neovascularizatoin, etc.) as well as those in which prevention is desired.

Nintedanib {Methyl (3Z)-3-{[(4-{methyl[(4-methylpiperazin-1-yl) acetyl]amino}phenyl)amino] (phenyl)methylidene}-2-oxo-2,3-dihydro-1H-indole-6-carboxylate} is a kinase inhibitor as described herein. Nintedanib inhibits primarily receptor tyrosine kinases including, for example vascular endothelial growth factor receptor (VEGFR 1-3), platelet-derived growth factor receptor (PDGFR $\alpha$ and $\beta$), fibroblast growth factor receptor (FGFR 1-4).

Formulations and Dosing Regimen

The methods described herein include the manufacture and use of pharmaceutical compositions, which include compounds identified by a method described herein as active ingredients. Also included are the pharmaceutical compositions themselves.

Pharmaceutical compositions typically include pharmaceutically acceptable excipients. As used herein the language "pharmaceutically acceptable excipient" or "pharmaceutically acceptable carrier" includes saline, solvents, dispersion media, coatings, antibacterial and antifungal agents, isotonic and absorption delaying agents, and the like, compatible with pharmaceutical administration.

The phrase "pharmaceutically acceptable salt" as used herein means those salts of a compound of interest that are safe and effective for administration to a mammal and that possess the desired biological activity. Pharmaceutically acceptable acid salts include, but are not limited to hydrochloride, hydrobromide, hydroiodide, nitrate, sulfate, bisulfate, phosphate, acid phosphate, I 0 isonicotinate, carbonate, bicarbonate, acetate, lactate, salicylate, citrate, tartrate, propionate, butyrate, pyruvate, oxalate, malonate, pantothenate, bitartarte, ascorbate, succinate, maleate, gentisinate, fumarate, gluconate, glucaronate, saccharate, formate, benzoate, glutamate, methanesulfonate, thanesulfonate, benzenesulfonate, p-toluenesulfonate and pamoate (i.e., I, I'rnethylene-bis-(2-hydroxy-3-naphthoate)) salts. Suitable base salts include, but are not limited to, 15 aluminum, calcium, lithium, magnesium, potassium, sodium, zinc, bismuth, and diethanolamine salts.

Methods of formulating suitable pharmaceutical compositions are known in the art, see, e.g., Remington: The Science and Practice of Pharmacy, 21st ed., 2005; and the books in the series Drugs and the Pharmaceutical Sciences: a Series of Textbooks and Monographs (Dekker, N.Y.). For example, solutions, suspensions, creams, ointments, Gels, gel-forming liquid, suspension containing liposomes or micelles, spray formulation, or emulsions used for ophthalmic application can include the following components: a sterile diluent such as water for injection, saline solution, fixed oils, polyethylene glycols, glycerin, propylene glycol or other synthetic solvents; antibacterial agents; antioxidants; chelating agents; buffers such as acetates, citrates or phosphates and agents for the adjustment of tonicity such as sodium chloride or dextrose. The pH can be adjusted with acids or bases, such as hydrochloric acid or sodium hydroxide.

The pharmaceutical composition disclosed herein may include a "therapeutically effective amount" of an agent described herein. Such effective amounts can be determined based on the effect of the administered agent, or the combinatorial effect of agents if more than one agent is used. A therapeutically effective amount of an agent may also vary according to factors such as the disease state, age, sex, and weight of the individual, and the ability of the compound to elicit a desired response in the individual, e.g., amelioration of at least one disorder parameter or amelioration of at least one symptom of the disorder. A therapeutically effective amount is also one in which any toxic or detrimental effects of the composition are outweighed by the therapeutically beneficial effects.

Effective doses of the compositions of the present disclosure, for the treatment of conditions vary depending upon many different factors, including means of administration, target site, physiological state of the subject, whether the subject is human or an animal, other medications administered, and whether treatment is prophylactic or therapeutic. Treatment dosages can be titrated using routine methods known to those of skill in the art to optimize safety and efficacy.

Pharmaceutical compositions suitable for injectable use can include sterile aqueous solutions (where water soluble) or dispersions and sterile powders for the extemporaneous preparation of sterile injectable solutions or dispersion. It should be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, and sodium chloride in the composition. Prolonged absorption of the injectable compositions can be brought about by including in the composition an agent that delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle, which contains a basic dispersion medium and the required other ingredients from those enumerated above. In the case of sterile powders for the preparation of sterile injectable solutions, the preferred methods of preparation are vacuum drying and freeze-drying, which yield a powder of the active ingredient plus any additional desired ingredient from a previously sterile-filtered solution thereof.

In one embodiment, the therapeutic compounds are prepared with carriers that will protect the therapeutic compounds against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Such formulations can be prepared using standard techniques, or obtained commercially.

The pharmaceutical compositions can be included in a container, pack, or dispenser together with instructions for administration.

Compositions and formulations of nintedanib, can be administered topically or as an injection of semi-solid formulation or solid implant, or by any other suitable methods known in the art. While it is possible to use the agent disclosed herein for therapy as is, it may be preferable to administer the agent as a pharmaceutical formulation, e.g., in admixture with a suitable pharmaceutical excipient, diluent, or carrier selected with regard to the intended route of administration and standard pharmaceutical practice. Pharmaceutical formulations include at least one active compound, in association with a pharmaceutically acceptable excipient, diluent, and/or carrier.

Administration of a composition or formulation can be once a day, twice a day, three times a day, four times a day or more often. Frequency may be decreased during a treatment maintenance phase of the treatment, e.g., once every second or third day instead of every day or twice a day. The dose and the administration frequency can be adjusted based on the judgment of the treating physician, for example, taking into account the clinical signs, pathological signs and clinical and subclinical symptoms of a disease of the conditions treated with the present methods, as well as the patient's clinical history.

It will be appreciated that the amount of an agent disclosed herein required for use in treatment will vary with the route of administration, the nature of the condition for which treatment is required, and the age, body weight and condition of the patient, and will be ultimately at the discretion of the attendant physician. Compositions will typically contain an effective amount of nintedanib. Preliminary doses can be determined according to animal tests, and the scaling of dosages for human administration can be performed according to art-accepted practices.

Length of treatment, i.e., number of days, will be readily determined by a physician treating the subject; however, the number of days of treatment may range from about 1 day to about 365 days. As provided by the present methods, the efficacy of treatment can be monitored during the course of treatment to determine whether the treatment has been successful, or whether additional (or modified) treatment is necessary.

Dosage, toxicity and therapeutic efficacy of the therapeutic compounds can be determined by standard pharmaceutical procedures in cell cultures or experimental animals, e.g., for determining the LD50 (the dose lethal to 50% of the population) and the ED50 (the dose therapeutically effective in 50% of the population). Dosage forms for nintedanib can be readily determined by the ordinarily skilled artisan, and can e.g., be obtained in animal models and in clinical studies reported in the literatures, for determining dosage, safety and efficacy according to standard methods known in the art. The exact formulation, route of administration and dosage can be chosen by the individual physician in view of the patient's condition.

Compositions for use in the present methods may include nintedanib at a concentration of 0.001% to 10% by weight or by volume the total amount of composition. For example, an aqueous composition comprises 0.001%, 0.01%, 0.1%, 0.5%, 1.0%, 1.5%, 2.0%, 5.0% or up to 10% nintedanib.

As will be familiar to those skilled in the art, administration to the eye of an aqueous solution may be in the form of "drop" or number of drops (e.g. of nintedanib solution) from a dropper or pipette or other dedicated sterile devices. Such drops will typically be up to 50 microliters in volume, but may be smaller e.g. less than 10 microliters.

EXAMPLES

The invention is further described in the following examples, which do not limit the scope of the invention described in the claims.

Example 1: Rabbit Cornea Suture Model

The rabbit cornea suture model of neovascularization demonstrates the method's ability to reduce abnormal corneal neovascularization.

Topical Ocular Formulations

Topical compositions comprising 0.2% or 0.05% nintedanib in 10% 2-hydroxypropyl beta cyclodextrin in phosphate buffer solution, pH 7.4 were prepared.

Animals and Treatment Procedure

Thirty female Zealand White rabbits were used to perform the study. Briefly, five sutures were placed in the upper cornea of the right eye of each animal on Day 1 to induce neovascularization. The animals were treated in both eyes with either drug, vehicle or saline as described in Table 1.

TABLE 1

| Dosing Period | Group | Treatment | Dosing Frequency | Number of Females |
|---|---|---|---|---|
| Days 1 to 7 | 1 | Saline | Once daily | 6 females |
| | 2 | Saline | Once daily | 6 females |
| | 3 | Saline | Once daily | 6 females |
| | 4 | Saline | Once daily | 6 females |
| | 5 | Saline | Once daily | 6 females |
| Days 8 to 15 | 1 | 0.2% nintedanib solution | BID | 6 females |
| | 2 | 0.2% nintedanib solution | TID | 6 females |
| | 3 | 0.05% nintedanib solution | BID | 6 females |
| | 4 | 0.05% nintedanib solution | TID | 6 females |
| | 5 | Saline (OD), Vehicle (OS) | TID | 6 females |

BID: Twice per day (approximately 10 to 12 hours apart).
TID: Three times per day (approximately 6 to 8 hours apart).
OD = right eye.
OS = left eye.
Both eyes were dosed, the dose volume was approximately 40 µL/eye.
Note:
The first dose of saline on Day 1 was done 4 hr post suture placement.

During the study, the animals were closely observed for various ocular indications as well as general physical conditions including body weight. Ocular images were taken on days 7, 10, 12, 14, 21, 28 for analysis of hyperemia.

Data Analysis

NIH ImageJ® software was used to analyze the ocular images. Each image was opened in ImageJ®, the scale was calibrated using the ruler in the photograph and the neovascularized area on the cornea near the suture was selected by the selection tool. The area in $mm^2$ was calculated by measurement tool in the software, recorded in excel and the image was captured and saved. Two-tailed t-TEST was used to determine whether pairs of groups are significantly different. The results were plotted as histograms of average with standard deviation for easy comparison.

Results and Discussions

Figure 2A:
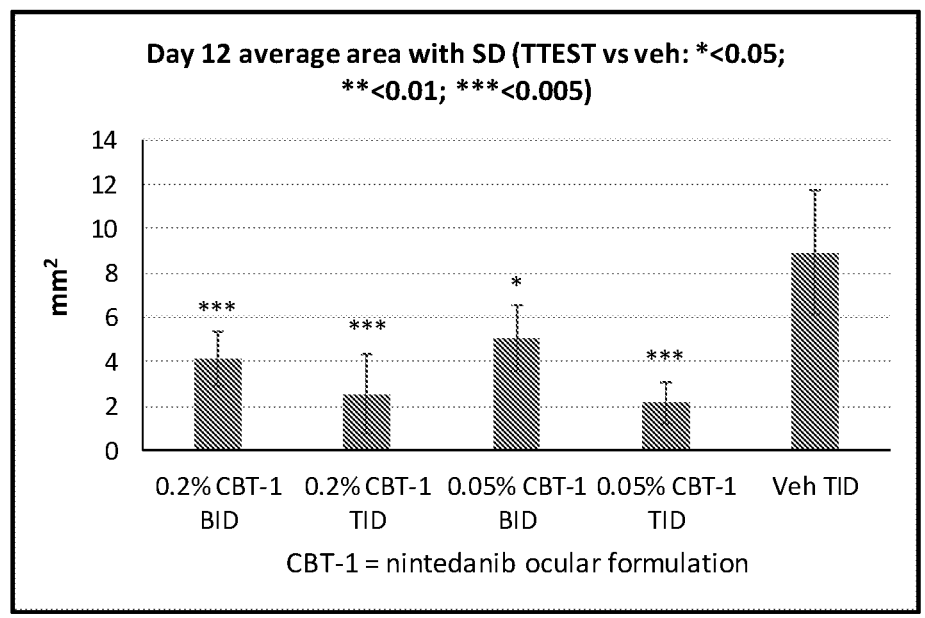
FIGS. 2A and 2B are graphs demonstrating the reduced cornea neovascularization in the presence of nintedanib in a rabbit cornea suture model.
Figure 2B:
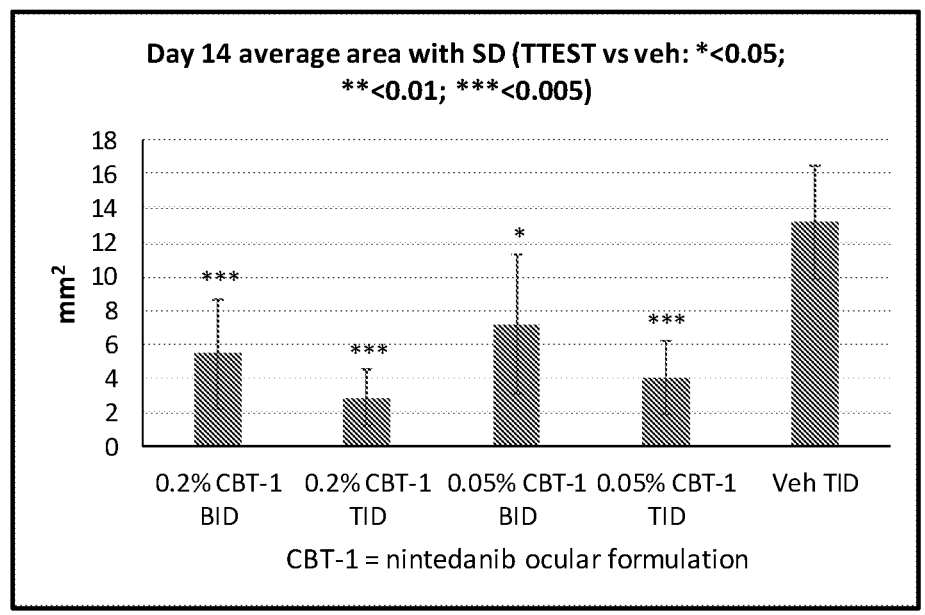

As shown in FIGS. 2A and 2B, nintedanib had a marked inhibitory effect on suture-induced neovascularization in the rabbit cornea 12 and 14 days after the suture induction. Higher dose of 0.2% nintedanib showed better efficacy than 0.05% nintedanib, while more frequent dosing regimen of TID dosing showed higher efficacy compared with BID dosing.

In summary, nintedanib strongly inhibited corneal neovascularization induced by suture. The strong activity is likely due to the special target profile of nintedanib that has potent activities against VEGFR1-3 and FGFR1-2. These results support the methods disclosed here.

Example 2: Mouse Corneal Graft Rejection Model

In this example, cornea of C57BL/6 mice would be transplanted onto BALB/c mice cornea as described (Sonoda et al. Invest Ophthalmol Vis Sci. 1995 February; 36(2):427-34; Invest Ophthalmol Vis Sci. 2000 March; 41(3):790-8; Yamagami et al. Invest Ophthalmol Vis Sci. 2001 May; 42(6):1293-8). The suture would be removed on day 7 after transplant. The mice would be divided into two groups. Group 1 would be treated with the nintedanib 0.2% solution and group 2 with the vehicle solution. Treatment would start immediately after transplant, TID for 8 weeks. The corneal opacity and graft rejection will be assessed weekly for 8 weeks as described.

The nintedanib treated group would show a significantly increased survival of the graft (lower rejection rate) over the 8 weeks of experiment. The result would indicate that the nintedanib 0.2% solution can prevent corneal graft rejection.

Example 3: Formulations

Nintedanib Ophthalmic Solution

The drug product is an isotonic ophthalmic solution prepared in 2-hydroxypropyl beta cyclodextrin or other similar cyclodextrins, and buffer solution, pH range from 5.5 to 8.0. Other viscosity, lubricant, preservative agents might be added to enhance functionality of the formulation. The compositions of the ophthalmic solution are disclosed in Table 2.

TABLE 2

Nintedanib Ophthalmic Solution

| Ingredients | Functions | Concentration Range (% w/v) |
|---|---|---|
| CBT-001 (Nintedanib free base) | Active Pharmaceutical Ingredient | 0.001-10 |
| Sodium carboxymethyl-cellulose | Viscosity Agent/dry eye relief | 0-1 |
| Pemulen TR | Viscosity Agent | 0-0.2 |
| Polyvinyl alcohol | Viscosity/Lubrication Agent | 0-1.5 |
| Hypromellose | Lubricant/dry eye relief | 0-1 |
| Carbomers | Lubricant/dry eye relief | 0-0.5 |
| Carmellose sodium | Lubricant/dry eye relief | 0-1 |
| Sodium hyaluronate | Lubricant/dry eye relief | 0-1.5 |
| Polyethylene glycol 400 | Lubricant/dry eye relief | 0-0.4 |
| Propylene glycol | Lubricant/dry eye relief | 0-0.6 |
| 2-hydroxypropyl beta cyclodextrin | Solubilizer | 0-10 |
| Sulfobutyl-beta-cyclodextrin | Solubilizer | 0-10 |
| Randomly methylated beta-cyclodextrin | Solubilizer | 0-5 |
| α-cyclodextrin | Solubilizer | 0-4 |
| β-cyclodextrin | Solubilizer | 0-1 |
| γ-cyclodextrin | Solubilizer | 0-1 |
| Poloxamer 188, or 237, or 407 | Solubilizer/lubricant | 0-5 |
| Polysorbate 80 | Solubilizer/lubricant/surfactant | 0-1 |
| Edetate disodium | Chelating Agent/Preservative | 0-0.01 |
| Benzalkonium chloride | Preservative | 0-0.02 |
| Sodium phosphate monobasic monohydrate | Buffer Agent | 0-0.43 |
| Sodium phosphate dibasic heptahydrate | Buffer Agent | 0-0.8 |
| Boric acid | Buffer Agent | 0-0.6 |
| Sodium borate, decahydrate | Buffer Agent | 0-0.045 |
| Citric acid, monohydrate | Buffer Agent/preservative | 0-0.13 |
| Sodium citrate, dihydrate | Buffer Agent/preservative | 0-0.45 |
| Glycerin | Tonicity Agent | 0-2.2 |
| Sodium chloride | Tonicity Agent | 0-0.83 |
| 1N Sodium hydroxide 1N Hydrochloric acid | pH Adjustment | pH 5.5-8.0 |
| Water for injection | Vehicle | Q.S. to 100 |

Nintedanib Ophthalmic Suspension

The drug product is an isotonic ophthalmic suspension prepared in carboxymethylcellulose sodium and buffer solution, pH range from 5.5 to 8.0. The drug particle sizes are reduced to below 40 micron. Other viscosity, lubricant, solubilizer, and preservative agents might be added to enhance functionality of the formulation suspension. The compositions are disclosed in Table 3.

TABLE 3

Nintedanib Ophthalmic Suspension

| Ingredients | Functions | Concentration Range (% w/v) |
|---|---|---|
| CBT-001 (Nintedanib free base) | Active Pharmaceutical Ingredient | 0.001-10 |
| Sodium carboxymethyl-cellulose | Viscosity Agent/dry eye relief | 0-1 |
| Pemulen TR | Viscosity Agent | 0-0.2 |
| Polyvinyl alcohol | Viscosity/Lubrication Agent | 0-1.5 |
| Hypromellose | Lubricant/dry eye relief | 0-1 |
| Carbomers | Lubricant/dry eye relief | 0-0.5 |
| Carmellose sodium | Lubricant/dry eye relief | 0-1 |
| Sodium hyaluronate | Lubricant/dry eye relief | 0-1.5 |
| Polyethylene glycol 400 | Lubricant/dry eye relief | 0-0.4 |
| Propylene glycol | Lubricant/dry eye relief | 0-0.6 |
| 2-hydroxypropyl beta cyclodextrin | Solubilizer | 0-10 |
| Sulfobutyl-beta-cyclodextrin | Solubilizer | 0-10 |
| Randomly methylated beta-cyclodextrin | Solubilizer | 0-5 |
| α-cyclodextrin | Solubilizer | 0-4 |
| β-cyclodextrin | Solubilizer | 0-1 |
| γ-cyclodextrin | Solubilizer | 0-1 |
| Poloxamer 188, or 237, or 407 | Solubilizer/lubricant | 0-5 |
| Polysorbate 80 | Solubilizer/lubricant/surfactant | 0-1 |
| Edetate disodium | Chelating Agent/Preservative | 0-0.01 |
| Benzalkonium chloride | Preservative | 0-0.02 |
| Sodium phosphate monobasic monohydrate | Buffer Agent | 0-0.43 |
| Sodium phosphate | Buffer Agent | 0-0.8 |

TABLE 3-continued

Nintedanib Ophthalmic Suspension

| Ingredients | Functions | Concentration Range (% w/v) |
|---|---|---|
| dibasic heptahydrate | | |
| Boric acid | Buffer Agent | 0-0.6 |
| Sodium borate, decahydrate | Buffer Agent | 0-0.045 |
| Citric acid, monohydrate | Buffer Agent/preservative | 0-0.13 |
| Sodium citrate, dihydrate | Buffer Agent/preservative | 0-0.45 |
| Glycerin | Tonicity Agent | 0-2.2 |
| Sodium chloride | Tonicity Agent | 0-0.83 |
| 1N Sodium hydroxide 1N Hydrochloric acid | pH Adjustment | pH 5.5-8.0 |
| Water for injection | Vehicle | Q.S. to 100 |

Nintedanib Ophthalmic Emulsion

The drug product is an isotonic ophthalmic emulsion. The drug is dissolved in the mixture oil phase and emulsifier excipients which is then emulsified and mixed with an aqueous phase with pH range from 5.5 to 8.0. Other viscosity, lubricant, solubilizer, and preservative agents might be added to enhance functionality of the emulsion formulation. The compositions are disclosed in Table 4.

TABLE 4

Nintedanib Ophthalmic Emulsion

| Ingredients | Functions | Concentration (% w/w) |
|---|---|---|
| CBT-001 (Nintedanib free base) | Active Pharmaceutical Ingredient | 0.001-10 |
| Castor oil | Oil solvent | 0-1.25 |
| Polyoxyl-40-Stearate | Emulsifier | 0-0.25 |
| Polysorbate 80 | Solubilizer/Emulsifier/Surfactant | 0-1 |
| Sulfobutyl-β-cyclodextrin | Solubilizer | 0-5 |
| 2-Hydroxypropyl-beta-cyclodextrin | Solubilizer | 0-5 |
| Randomly methylated beta-cyclodextrin | Solubilizer | 0-5 |
| α-cyclodextrin | Solubilizer | 0-4 |
| β-cyclodextrin | Solubilizer | 0-1 |
| γ-cyclodextrin | Solubilizer | 0-1 |
| Glycerin | Tonicity Agent | 0-2.2 |
| Sodium Chloride | Tonicity Agent | 0-0.83 |
| Pemulen TR2 | Viscosity Agent | 0-0.1 |
| Sodium carboxymethyl-cellulose | Viscosity Agent | 0-0.5 |
| Polyvinyl alcohol | Viscosity/Lubrication Agent | 0-1.5 |
| Hypromellose | Lubricant/dry eye relief | 0-1 |
| Carbomers | Lubricant/dry eye relief | 0-0.5 |
| Carmellose sodium | Lubricant/dry eye relief | 0-1 |
| Sodium hyaluronate | Lubricant/dry eye relief | 0-1.5 |
| Polyethylene glycol 400 | Lubricant/dry eye relief | 0-0.4 |
| Propylene glycol | Lubricant/dry eye relief | 0-0.6 |
| Poloxamer 188, or 237, or 407 | Solubilizer/lubricant | 0-5 |
| Boric acid | Buffer | 0-0.6 |
| Sodium borate, decahydrate | Buffer | 0-0.045 |
| Citric acid, monohydrate | Buffer/preservative | 0-0.13 |
| Sodium citrate, dihydrate | Buffer/preservative | 0-0.45 |
| Sodium phosphate, monobasic monohydrate | Buffer | 0-0.43 |
| Sodium phosphate dibasic heptahydrate | Buffer | 0-0.8 |
| 1N & 5N Sodium hydroxide 1N Hydrochloric acid | pH Adjustment | pH 5.5-8.0 |
| Water for injection | Aqueous Vehicle | Q.S. 100 |

Nintedanib Sustained Release Semi-Solid Formulation

The drug product is an isotonic sustained release semi-solid formulation. The drug is dissolved and/or suspended in a semi-solid medium with pH range from 5.5 to 8.0. Other viscosity, lubricant, solubilizer, and preservative agents might be added to enhance functionality of the sustained release semi-solid formulation. The compositions are disclosed in Table 5.

TABLE 5

Sustained Release Semi-Solid Formulation

| Ingredients | Functions | Concentration (% w/w) |
|---|---|---|
| CBT-001 (Nintedanib free base) | Active Pharmaceutical Ingredient | 0.001-10 |
| Xanthan Gum | Viscosity/Thickener | 0-10 |
| Hydroxypropyl methylcellulose | Viscosity/Thickener | 0-10 |
| Sodium hyaluronate | Viscosity/Thickener | 0-5 |
| Hyaluronic acid | Viscosity/Thickener | 0-5 |
| Boric acid | Buffer | 0-0.6 |
| Sodium borate, decahydrate | Buffer | 0-0.045 |
| Citric acid, monohydrate | Buffer/preservative | 0-0.13 |
| Sodium citrate, dihydrate | Buffer/preservative | 0-0.45 |
| Sodium phosphate, monobasic monohydrate | Buffer | 0-0.43 |
| Sodium phosphate dibasic heptahydrate | Buffer | 0-0.8 |
| 1N & 5N Sodium hydroxide 1N Hydrochloric acid | pH Adjustment | pH 5.5-8.0 |
| Water for injection | Aqueous Vehicle | Q.S. 100 |

Nintedanib Sustained Release Implants

The drug product is a solid implant. The drug is mixed and blended with one or more polymers. The mixture of drug and polymers is melted at a predetermined temperature and extruded into a filament with a predetermined diameter size. The formulation filament is cut into a predetermined size of segment which can be implanted into ocular tissues. The compositions are disclosed in Table 6.

TABLE 6

Sustained Release Implants

| Ingredients | Functions | Concentration (% w/w) |
|---|---|---|
| CBT-001 (Nintedanib free base) | Active Pharmaceutical Ingredient | 0.001-10 |
| Poly (D,L-Lactide), i.v. 0.25-0.35 dL/g | Polymer | 0-100 |
| Poly (D,L-Lactide-coglycolide) i.v. 0.14-0.22 dL/g | Polymer | 0-100 |
| Poly (D,L-Lactide), i.v. 0.16-0.25 dL/g | Polymer | 0-100 |
| Polyethylene Glycol 3350 | Polymer | 0-20 |
| Resomer ®RG755S | Polymer | 0-100 |
| Resomer ®RG753H | Polymer | 0-100 |

Without limitation, an example composition, for use in the methods according to the invention, may be modified from existing ophthalmically acceptable compositions.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for treating, preventing, or delaying onset of corneal graft rejection after corneal transplant, comprising administering to an eye of a subject that has undergone corneal transplant an effective amount of a compound selected from the group consisting of axitinib, cediranib, linifanib, motesanib, nintedanib, pazopanib, regorafenib, sunitinib, tivozanib, or a pharmaceutically acceptable salt thereof.

2. The method of claim 1, wherein the compound is administered in an amount effective to prevent graft rejection by inhibiting abnormal neovascularization and inflammation in the eye of the subject.

3. The method of claim 1, wherein the subject has a condition selected from the group consisting of graft versus host disease, atopic conjunctivitis, ocular rosacea, ocular pemphigoid, Lyell's syndrome, contact lens induced neovascularization, ulceration, alkali burns, stem cell deficiency, pinguecula, neovascular glaucoma, dry eye disease, Sjogren's syndrome, Meibomian gland dysfunction, Steven Johnson syndrome, tumor in the eye, and neovascularization induced by viral, bacterial, fungal, or parasitic infection.

4. The method of claim 1, wherein the compound is administered in the form of topical ocular formulation or ocular implant.

5. The method of claim 4, wherein the ocular implant is in the form of a semi-solid or solid sustained-release implant.

6. The method of claim 5, wherein the implant is injected into the eye of the subject.

7. The method of claim 4, wherein the topical ocular formulation is a topical eye drop.

8. The method of claim 4, wherein the topical ocular formulation is a solution, suspension, cream, ointment, gel, gel-forming liquid, suspension containing liposomes or micelles, spray formulation, or emulsion.

9. The method of claim 1, further comprising administering to the eye of the subject an effective amount of an antimetabolite.

10. The method of claim 9, wherein the antimetabolite is selected from the group consisting of mycophenolate mofetil, methotrexate, mitomycin C, 5-fluorouracil, azathioprine, and thiotepa.

* * * * *

UNITED STATES PATENT AND TRADEMARK OFFICE
CERTIFICATE OF CORRECTION

| | |
|---|---|
| PATENT NO. | : 11,246,864 B2 |
| APPLICATION NO. | : 16/306152 |
| DATED | : February 15, 2022 |
| INVENTOR(S) | : Jinsong Ni and Rong Yang |

It is certified that error appears in the above-identified patent and that said Letters Patent is hereby corrected as shown below:

On the Title Page

Column 2 (Other Publications), Line 3, delete "10(l):68-85." and insert -- 10(1):68-85. --.

Signed and Sealed this
Fifth Day of July, 2022

Katherine Kelly Vidal
*Director of the United States Patent and Trademark Office*